United States Patent
Brandl et al.

(10) Patent No.: US 6,814,869 B2
(45) Date of Patent: Nov. 9, 2004

(54) METHOD AND AN APPARATUS AS WELL AS A CONNECTOR AND A CONCENTRATE CONTAINER UNIT FOR THE PREPARATION OF SOLUTIONS

(75) Inventors: Matthias Brandl, Bad Koenigshofen (DE); Peter Hilgers, Schonungen (DE); Franz Kugelmann, St. Wendel (DE); Matthias Meisinger, Spiesen-Elversberg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 128 days.

(21) Appl. No.: 10/200,511

(22) Filed: Jul. 23, 2002

(65) Prior Publication Data

US 2003/0024880 A1 Feb. 6, 2003

(30) Foreign Application Priority Data

Jul. 25, 2001 (DE) .......................................... 101 36 262

(51) Int. Cl.⁷ .............................................. B01D 61/30
(52) U.S. Cl. ............................... 210/652; 137/2; 137/5; 137/561 A; 210/321.71; 210/257.2; 210/646; 285/125.1
(58) Field of Search ........................ 210/96.2, 97, 139, 210/257.2, 321.69, 321.71, 636, 646, 647, 652; 137/2, 5, 88, 268, 561 A, 797; 285/128.1, 125.1; 422/264

(56) References Cited

U.S. PATENT DOCUMENTS

| | | | | | |
|---|---|---|---|---|---|
| 4,784,495 | A | * | 11/1988 | Jonsson et al. | 366/151.1 |
| 5,511,875 | A | * | 4/1996 | Jonsson et al. | 366/136 |
| 5,547,645 | A | * | 8/1996 | Ego et al. | 422/264 |
| 5,972,223 | A | * | 10/1999 | Jonsson et al. | 210/647 |
| 6,136,201 | A | * | 10/2000 | Shah et al. | 210/739 |

FOREIGN PATENT DOCUMENTS

| | | |
|---|---|---|
| DE | 196 05 260 | 11/1996 |
| EP | 0 197 553 | 10/1986 |

* cited by examiner

*Primary Examiner*—Joseph Drodge
(74) *Attorney, Agent, or Firm*—Jacobson Holman PLLC

(57) ABSTRACT

A method and apparatus for the preparation of solutions to be manufactured from at least two concentrates and a solvent. After placing of two concentrate holders into associated recipients, both concentrate holders are connected using a single connector having two connection states. In a first connection state, solvent flows to the first concentrate holder, with the solution being led into a collection holder and, after the flushing of the concentrate from the first concentrate holder, the connector moves to a second connection state in which an automatic connecting of the second concentrate holder takes place, whereupon solvent flows through the second concentrate holder and the solution is likewise supplied to the collection holder.

18 Claims, 4 Drawing Sheets

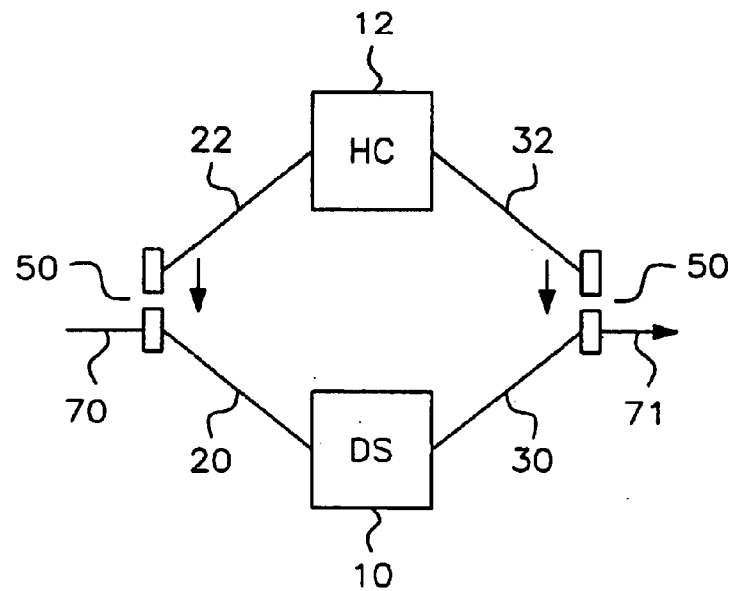
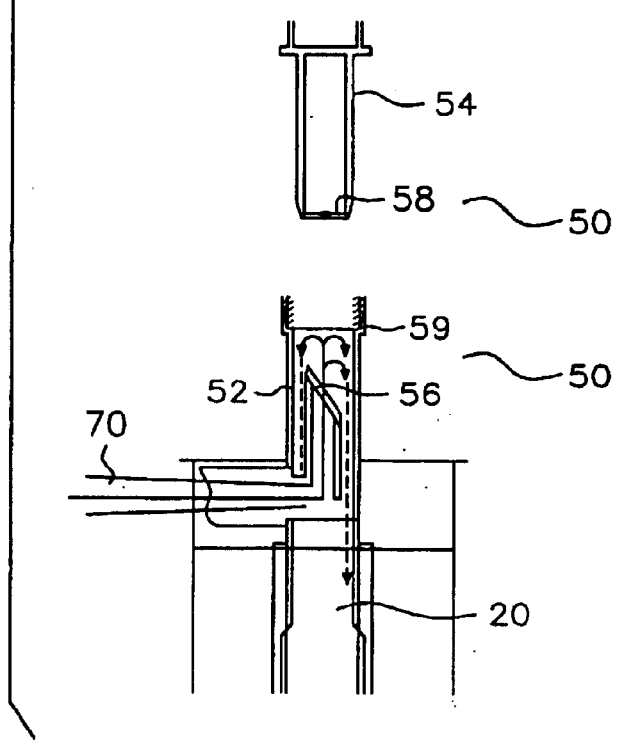

METHOD AND AN APPARATUS AS WELL AS A CONNECTOR AND A CONCENTRATE CONTAINER UNIT FOR THE PREPARATION OF SOLUTIONS

BACKGROUND OF THE INVENTION

1. Field of the Invention

The present invention relates to a method and an apparatus for the preparation of solutions to be manufactured from at least two concentrates and a solvent as well as to a connector and to a concentrate container unit containing a concentrate.

2. Description of the Related Art

An important application possibility for such a method or for such an apparatus is dialysis in which high purity haemodialysis solutions are required which have to be made available in compositions and concentrations matched to the patients. The haemodialysis solutions are usually manufactured from two concentrates which a re stored in separate containers and only mixed in the course of the manufacture of the haemodialysis solution.

SUMMARY OF THE INVENTION

In the manufacture of haemodialysis solutions it must absolutely be ensured that no errors are made since incorrect compositions of the haemodialysis solution or incorrect concentrations of the components contained therein can result in a substantial risk for the patent to be treated as part of the dialysis.

Batch systems are known in which the medical staff making the haemodialysis solution available fill the different concentrates required for the manufacture into a flushing vessel. These are subsequently separated from pre-heated high purity water or are mixed with this and flushed into a receiving vessel which is subsequently taken to the site of the treatment to be carried out. While the control of the finished haemodialysis solution can take place by a conductivity measurement, errors in the preparation of the haemodialysis solution can in particular not be precluded if the incorrect solution and the desired solution have similar conductivity values.

It is therefore the object of the present invention to further develop a method and an apparatus for the preparation of solutions to be manufactured from at least two concentrates and a solvent such that it is simplified and the occurrence of errors in the preparation of the solution is further reduced.

This object is solved by a method for the preparation of solutions to be manufactured from at least two concentrates and a solvent in which, after the placing of concentrate holders into associated recipients, the connection takes place of a first concentrate holder to a solvent source, solvent flows through the first concentrate holder and the solution is led into a collection holder. After the flushing of the concentrate from the first concentrate holder, an automatic connecting of a second concentrate holder takes place, whereupon solvent flows through the second concentrate holder and the solution is likewise supplied to the collection holder.

The object is further solved by an apparatus for the preparation of solutions to be manufactured from at least two concentrates and a solvent having at least two concentrate holders. The apparatus includes feed lines through which the solvent can be led to the concentrate holders, discharge lines by means of which the solutions can be led from the concentrate holders into a collection holder, a connector which connects a solvent source to the first concentrate holder in a first position and the solvent source to the second concentrate holder in a second position, and means by which the connector is movable from the first into the second position.

The object is also solved by a concentrate container unit having a solid or a liquid concentrate received in a concentrate holder and having two first connector elements or two second connector elements. The first connector elements have a membrane closing them and a piercing pin which is in connection with a connection line and which is surrounded by an annular space being in connection with the concentrate holder. The second connector elements are in connection with the concentrate holder and have a membrane closing the second connector elements.

In the method in accordance with the invention, after concentrate holders have been placed into associated receivers, the connection is made of a first concentrate holder to a solvent source; subsequently, solvent flows through the first concentrate holder and the solution is led into a collection holder. After the flushing of the concentrate from the first concentrate holder, an automatic connecting of a second concentrate holder takes place, whereupon solvent flows through the second concentrate holder and the solution is likewise led to the collection holder. In a first preparation phase, the through-flow, and thus the dissolution of the concentrate, takes place exclusively through the first concentrate holder. After the automatic connection of the second concentrate holder, this is flowed through. The substances contained therein are dissolved and likewise flushed out.

The present invention lowers the risk of operator error by automating the addition of concentrate. After the flushing of the concentrate from the first concentrate holder, an automatic switch to the second concentrate holder takes place, whereupon this is flowed through and the solution is likewise led to the collection holder. The operator comfort in such a method is very high due to the simple handling, i.e. the minimization of user steps. User interactions during the preparation time are avoided.

The solvent can be high purity water manufactured by reverse osmosis. A dry concentrate containing NaCl, $NaHCO_3$ and glucose can be present in the first concentrate holder and a liquid concentrate can be present in the second concentrate holder, said liquid concentrate containing as main components the ions $K^+$, $Ca^{2+}$, $Mg^{2+}$ and NaCl. Ultra pure haemodialysis solution can be reliably manufactured in this way.

Provision is made in another aspect of the present invention for the automatic connecting of the second concentrate holder to take place when a defined period of time since the start of the flowing through of the first concentrate holder has elapsed, when the conductivity of the solution leaving the first concentrate holder has fallen below a threshold value or when the level in the collection holder has exceeded a pre-determined value. A control unit is accordingly provided in this case which carries out a comparison between the corresponding actual value and a nominal value or limiting value and initiates the automatic connecting of the second concentrate holder when the nominal value or limiting value is reached.

Provision is made in another aspect of the present invention for an automatic flow diversion of the first concentrate holder to take place simultaneously with the automatic connecting of the second concentrate holder.

Confusion is precluded due to the clearly pre-determined order of the concentrate addition. Moreover, the case cannot occur that the one concentrate is added a number of times by accident or that the other concentrate is added a number of times by accident. Nor can the case occur that one of the concentrates is omitted by accident, since the present invention ensures that an automatic connecting and subsequent flowing through of the second concentrate holder takes place after the flushing of the concentrate from the first concentrate holder.

The present invention further relates to an apparatus for the preparation of solutions to be manufactured from at least two concentrates and a solvent. The apparatus has at least two concentrate holders as well as feed lines through which the solvent can be led to the concentrate holders, discharge lines by means of which the solutions can be led from the concentrate holders into a collection holder, a connector which, in a first position, connects a solution source to the first concentrate holder and, in a second position, connects the solution source to the second concentrate holder, and finally means by which the connector is movable from the first position into the second position. After the placing of the concentrate holders into the apparatus in accordance with the invention, or into the receivers of the apparatus provided therefor, the time sequence and the connection and the flow regulation take place automatically. The work of the user is accordingly reduced to putting in the desired concentrate holders.

A connector which can be moved into two positions is known, for example, from EP 0 197 553 A2. The connector disclosed therein is used in transperitoneal dialysis and, depending on the connector position, allows the flow from a dialysis pouch to the patient, into an empty pouch or also the flow from the patient into the empty pouch. The connector has a female connector piece which is connected to a peritoneal catheter via a line. This connector piece can be connected to a male connector piece to allow the inflow of fresh haemodialysis solution from a full pouch into the peritoneal cavity. An empty pouch is connected to the male connector piece via a further line. The female connector piece has a cut-off member which is opened at a pre-set connection status of the connector by a central hose piece of the male connector piece. A fluid connection with both pouches and with the peritoneal cavity is made possible due to the arrangement of a second connection at the male connector piece in interaction with the cut-off member of the female connector piece made as a membrane and with a radial opening in the central hose piece.

It is particularly advantageous for the concentrate holders to be made as disposable articles and to be provided in each case with two self-sealing connector elements. The use of disposable elements provides the advantage that these are of a favourable cost. Due to the self-sealing connections, the concentrate holders are closed before and during the application, whereby operator errors and an incorrect preparation of the solution are prevented and an aseptic state of the haemodialysis solution to be manufactured is ensured. Each of the concentrate holders has two respective connector elements which, depending on the arrangement, allow the inflow into the concentrate holders or the discharge from the concentrate holders.

In another aspect of the present invention, provision is made for the concentrate holders to be made in funnel form. Such a design of the containers allows the optimum and full dissolution of the concentrates and, in addition, in corresponding connection with a discharge line, the complete emptying of the concentrate holders. The advantage thereby results that at best a minimum residual volume remains in the disposable articles after use.

In another aspect of the present invention, provision is made for the connector to have a first connector element being in connection with a first concentrate holder, with a second connector element being connected to a second concentrate holder being able to be inserted into said first connector element, and for a piercing pin to be provided in the first connector element by means of which a membrane closing the second connector element can be cut on the movement of the connector into the second position. Provision is additionally made for the first connector element to have a membrane, preferably a silicone membrane, which terminates it. The membranes are intact before the second concentrate holder is flowed through and only the first concentrate holder is flowed through. In the connection process, the said silicone membrane is first pierced. A sealing connection to the second concentrate holder is thus initially manufactured. Finally, in a further phase of the connection process, the membrane closing the second connector element is pierced by the piercing pin, which results in the flow of the solvent now mainly being led through the second concentrate holder. In this connection, it is favourable, but not necessary, for the flow through the first concentrate holder to be completely suppressed.

In a preferred aspect of the present invention, a connection line is provided which is arranged at the first connector part and through which the solvent can be led from the solvent source to the connector or the solution from the connector to the collection holder.

An annular space can extend around the piercing pin of the first connector element and form a part of the feed line or of the discharge line which connects the connector to the first concentrate holder. Before the connecting, the solvent is guided through the piercing pin and subsequently through the annular space which forms a first part of the feed line which leads to the first concentrate holder. After the connection, the annular space is filled by the second connector element and the solvent is now guided through the piercing pin through the second connector element into the second concentrate holder.

The present invention further relates to a connector having a first connector element which is in connection with or can be connected to a first concentrate holder and having a second connector element which is in connection with or can be connected to a second concentrate holder, with the first connector element being closed by a membrane which can be cut by the second connector element insertable into the first connector element and with the first connector element having a piercing pin by means of which a membrane closing the second connector element can be cut.

The present invention further relates to a concentrate container unit having a solid or liquid concentrate accommodated in a concentrate holder and having two first or two second connector elements, with the first connector elements having a membrane closing them and a piercing pin being in connection with a connection line, said piercing pin being surrounded by an annular space being in connection with the concentrate holder and with the second connector elements being in connection with the concentrate holder and having a membrane closing the second connector elements. The concentrate container unit is advantageously made as a disposable article.

The concentrate container unit can comprise an inflow line and a discharge line which extend from the first and second connector elements to the concentrate holder or from this to the first and second connector elements.

In another aspect of the present invention, provision is made for the membrane closing the first and/or the second connector element to be a silicone membrane.

The concentrate can be a dry concentrate containing NaCl, NaHO₃ and glucose or a liquid concentrate which contains as the main components the ions $K^+$, $Ca^{2+}$, $Ng^{2+}$ and NaCl. The liquid concentrate can furthermore contain the components and HCl.

BRIEF DESCRIPTION OF THE DRAWINGS

Further details and advantages will be explained in more detail with reference to an embodiment illustrated in the drawing. There are shown:

FIG. 2 shows a schematic representation of the flow through the first concentrate holder directly before the connection of the second concentrate holder;

FIG. 3 shows a schematic representation of the design of the connector with a first and a second connector element;

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1A:
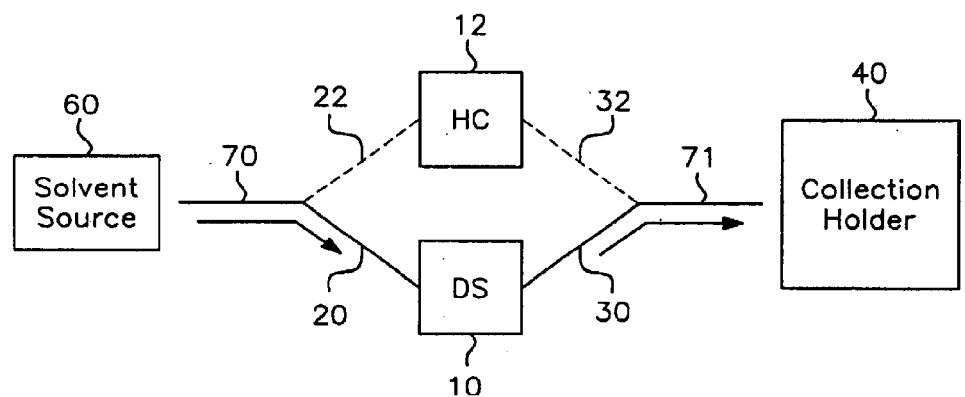
FIGS. 1A and 1B show a schematic representation of the flow through a first concentrate holder with the concentrate DS in a first filling phase and subsequently through a second concentrate holder with the concentrate HC in a second filling phase.
Figure 1B:
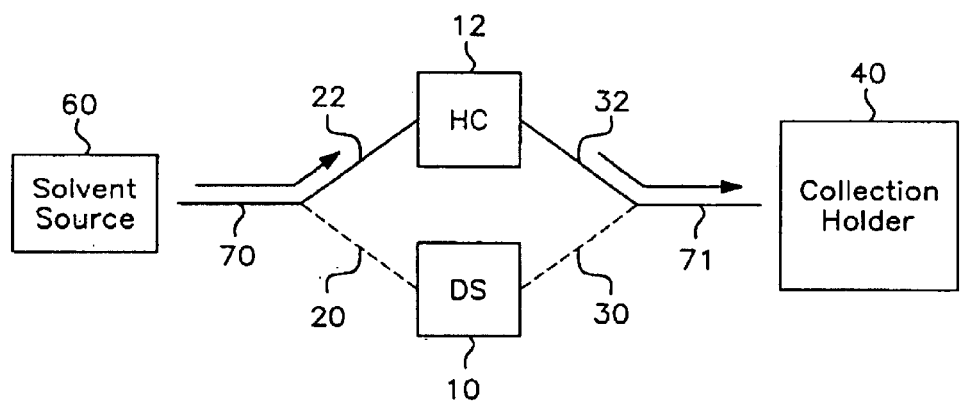

FIG. 1A shows the first filling phase in which high purity water is guided from the solvent source 60 (RO plant) into the first concentrate holder 10. The dry concentrate DS is disposed in this which contains NaCl, NaHCO₃ and glucose. The two concentrate holders 10, 12 are provided with feed lines 20, 22 which are flowed through subsequent to the connection line 70 and through which the solvent can be led to the concentrate holders 10, 12. Furthermore, discharge lines 30, 32 are provided by means of which the solvents are guided from the concentrate holders 10, 12 via a connection line 71 into the collection holder 40. The solution leaving the first concentrate holder 10 is fed to a collection holder 40 which is made as a pouch here. At a pre-set time, the automatic connecting of the second concentrate holder 12 takes place in which the liquid concentrate HC is present which contains as the main components the ions $K^+$, $Ca^{2+}$, $Mg^{2+}$ and NaCl. In addition, citrate and HCl can be present herein. The solvent now flows from the solvent source 60 through the second concentrate holder 12 into the collection container 40. This state is shown in FIG. 1B as the second filling phase.

The two concentrate holders 10, 12 are designed as low-cost disposable articles (disposables). The concentrate holders are each provided with two connector elements which connect in a self-sealing manner. The concentrate holders 10, 12 are made in funnel form and, due to the arrangement of a discharge line in the lower region of the funnel, allow a largely full emptying and thus an optimum utilisation of the concentrates.

The concentrate holders 10, 12 are closed before and during the application, thus preventing operator errors and errors in the solution preparation and guaranteeing the aseptic manufacture of the haemodialysis solution.

Another advantage of the present method is that no valves have to be used for the flow regulation since an automatic flow diversion takes place due to the connection.

The concentrate disposed in the concentrate containers 10 and 12 can be present in liquid form or in solid form.

Since the correct addition of the concentrates takes place automatically, the work of the user is restricted to the placing of the concentration holders 10, 12 into a corresponding receiving apparatus. The time sequence as well as the connection and the flow regulation take place automatically. Whereas with already known solutions, a flow regulation has to take place by rotary valves, by hose crimping valves or also by globe valves which are complex in design and which give rise to a risk of operator error by the user, the present invention manages without such aids. Connectors are sufficient which ensure an automatic connecting of the second concentrate holder 12 to the solvent source 60 or to the collection holder 40 at the desired time.

FIG. 2 again shows the schematic representation of the flow of the solvent through the first concentrate holder 10 directly before connection of the second concentrate holder 12. Both connectors 50 are moved at the pre-set time into their second position in which the second concentrate holder 12 is now flowed through.

FIG. 3 shows a detailed representation of an embodiment of a connector 50 in accordance with the invention which can be moved from a first position into a second position. The connector 50 has a first connector element 52 which is in connection with the first concentrate holder 10. A second connector element 54, which can be inserted into the first connector element 52, is in connection with the second concentrate holder 12. A piercing pin 56 is provided in the first connector element 52 and a membrane 58 closing the second connector element 54 can be separated by means of this on the movement of the connector 50 into the second position. The first connector element 52 is closed by a silicone membrane 59. In the position shown in FIG. 3, solvent is finally led through the connection line 70 and through the piercing pin 56 into the feed line 20 of the first concentrate holder 10 or, in the reverse direction, through a corresponding discharge line and through the piercing pin into a corresponding connection line. At a pre-set time, a switch is made to the second connection state, with first the silicone membrane 59 being cut, whereupon an impervious connection to the second concentrate holder 12 is manufactured. As the putting together continues, the membrane 58 is cut by means of the piercing pin 56 and the second connector element 54 is introduced into the annular space extending around the piercing pin 56. The solvent is now led through the connection lead 70, the piercing pin 56 and the second connector element 54 into the corresponding feed line of the second concentrate holder 12. The solution being discharged from the second concentrate holder 12 is correspondingly led in the opposite direction.

The above described connection process of the connector elements 52, 54 takes place on the inflow side and on the outflow side. The first concentrate holder 10 is preferably provided with two first connector elements 52 and the second concentrate holder 12 is provided with two second connector elements 54. At the time of the flow switchover, both connectors 50 are now actuated, i.e. the connector elements 52, 54 are put together both on the inflow side and on the outflow side, so that the second concentrate holder is now flowed through.

Figure 4C:
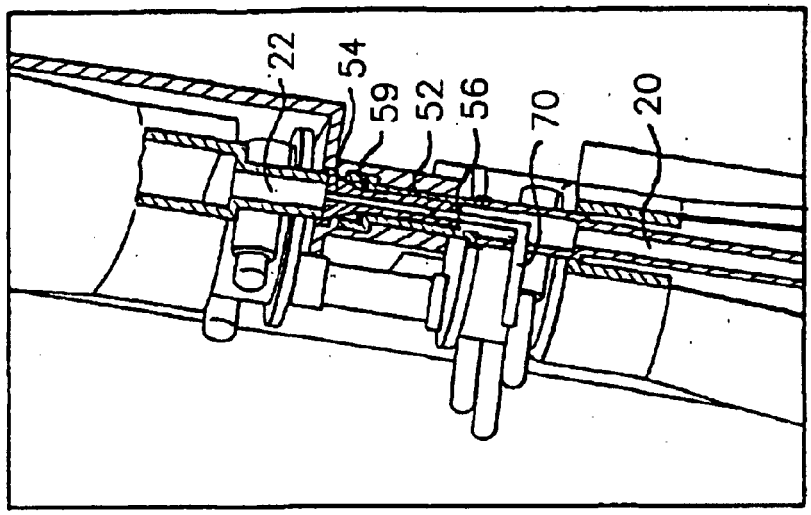
FIGS. 4A, 4B and 4C are representations of different connector positions before and after the connection of the second concentrate holder.
Figure 4B:
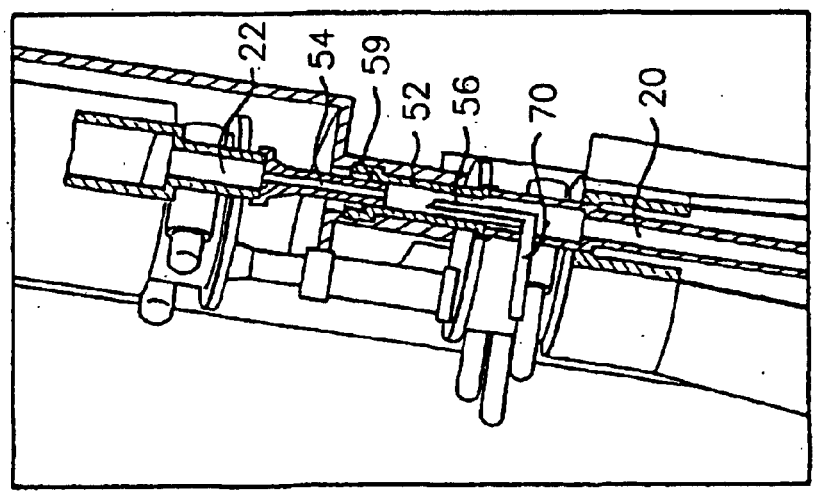
Figure 4A:
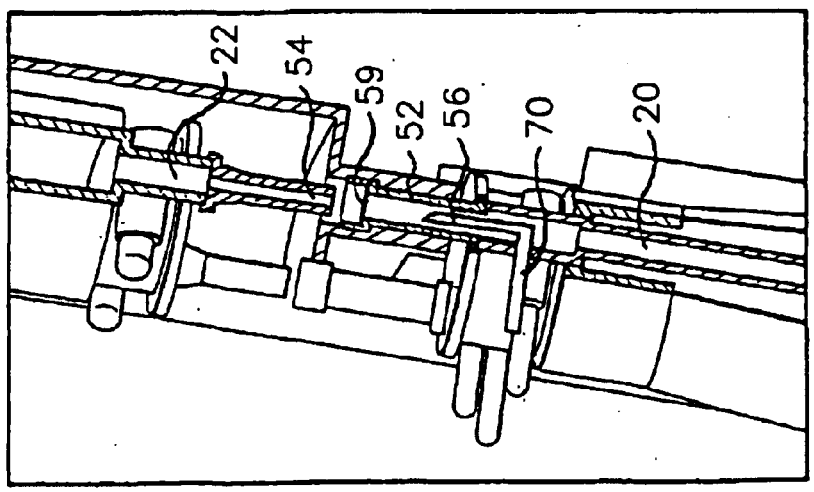
Figure 5:
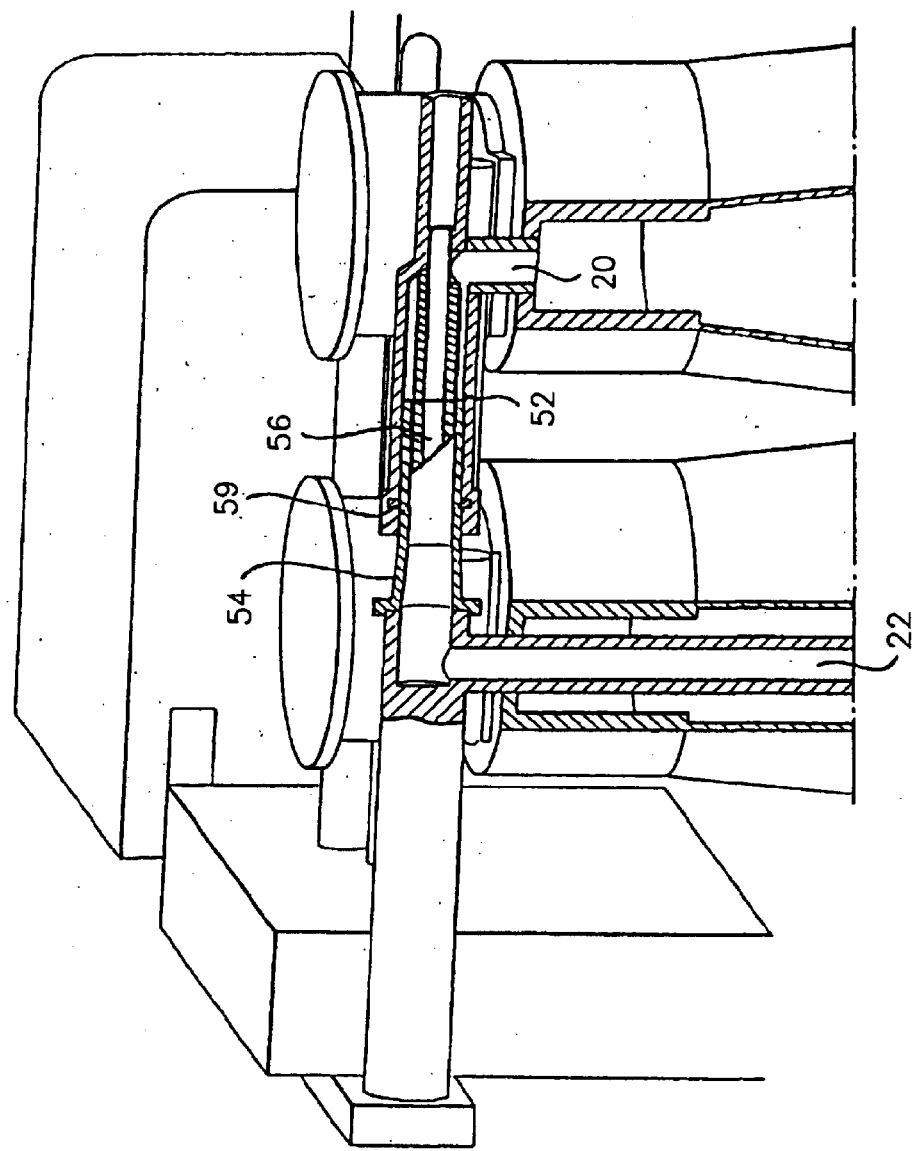
FIG. 5 shows a connector arrangement in accordance with FIG. 4 in a horizontal design.

The connection process just described is represented again in FIGS. 4A, 4B, 4C and FIG. 5. FIGS. 4A, 4B, and 4C show a corresponding connecting of a first and of a second concentrate holder in a vertical arrangement and FIG. 5 in a horizontal arrangement. FIG. 4A shows the connector 50 in a first position in which the solvent source is in connection with the first concentrate holder via the connection line 70, the piercing pin 56 and the feed line 20. FIG. 4B shows the connection status in which a sealing connection to the second concentrate holder has already been made in that the second connector element 54 has been introduced into the first connector element 52 after the cutting of the membrane 59. It results from the position shown in FIG. 4C that the piercing pin 56 has cut the membrane 58 closing the second connector element 54 (see FIG. 3), whereby a fluid impervious connection has been manufactured to the second concentrate holder. The solvent now flows through the feed line 22 into the second concentrate holder.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for the preparation of solutions to be manufactured from at least two concentrates and a solvent comprising, after placing first and second concentrate holders into associated recipients, connecting the first concentrate holder to a solvent source so that solvent flows through the first concentrate holder and a resulting solution is led into a collection holder; and, when a threshold value has been met following connection of the first concentrate holder to the solvent source, automatically connecting the second concentrate holder to said solvent source so that the solvent flows through the second concentrate holder and a second resulting solution is likewise supplied to the collection holder, said steps of connecting the first concentrate holder to the solvent source and thereafter automatically connecting the second concentrate holder to said solvent source being performed using a single self-sealing connector.

2. A method in accordance with claim 1, wherein the solvent is high purity water manufactured by reverse osmosis and wherein a dry concentrate containing NaCl, $NaHCO_3$ and glucose is present in the first concentrate holder and a liquid concentrate containing the ions $k^3$, $Ca^{2+}$, $Mg^{2+}$ and NaCl is present in the second concentrate holder.

3. A method in accordance with of claim 1, wherein the threshold value for automatic connecting of the second concentrate holder is met when a defined time period has elapsed since the start of solvent flow through the first concentrate holder.

4. A method in accordance with claim 1, wherein an automatic flow diversion of the first concentrate holder takes place simultaneously with the automatic connecting of the second concentrate holder.

5. A method in accordance with of claim 1, wherein the threshold value for automatic connecting of the second concentrate holder is met when the conductivity of the solution being discharged from the first concentrate holder has fallen below a limiting value.

6. A method in accordance with of claim 1, wherein the threshold value for automatic connecting of the second concentrate holder is met when the level in the collection holder has exceeded a pre-determined value.

7. An apparatus for the preparation of solutions to be manufactured from at least two concentrates and a solvent comprising: at least two concentrate holders feed lines through which the solvent is directed to the concentrate holders discharge lines by means of which solutions are directed from the concentrate holders into a collection holder and a single self-sealing connector which connects a solvent source to the first concentrate holder in a first position and the solvent source to the second concentrate holder in a second position, movement from the first position into the second position occurring automatically when a threshold value is met.

8. An apparatus in accordance with claim 7, wherein the concentrate holders 1 are disposable articles and are each provided with two self-sealing connector elements.

9. An apparatus in accordance with claims 7, wherein the concentrate holders are made in funnel-like form.

10. An apparatus in accordance with claim 7, wherein the connector has a first connector element in connection with the first concentrate holder and a second connector element in connection with the second concentrate holder, said second connector element being inserted into said first connector element and a piercing pin provided in the first connector element cutting a membrane closing the second connector element upon movement of the connector into the second position.

11. An apparatus in accordance with claim 10, wherein a first connection line is provided which is arranged at the first connector element and through which the solvent is directed from the solvent source to the connector, and a second connection line is provided by which the resulting solution is directed the from the connector to the collection holder.

12. An apparatus in accordance with claim 10, wherein an annular space extends around the piercing pin of the first connector element, said annular space forming a part of a feed line or of a discharge line which connects the connector to the first concentrate holder.

13. A connector comprising a first connector element which is connected to a first concentrate holder and a second connector element connected to a second concentrate holder such that said connector connects both said first and second concentrate holder, said first connector element having therein a piercing pin and being closed by a first membrane spaced from said pin, said second connector element being closed by a second membrane, said second connector element cutting said first membrane when at least partly inserted into the first connector element, and the piercing pin of said first connector element thereafter cutting said second membrane when said second connector element is fully inserted within said first connector element.

14. A concentrate container unit having a solid or a liquid concentrate received in a first concentrate holder and a second concentrate holder, said first concentrate holder having two first connector elements and said second concentrate holder having two second connector elements, each of said first connector elements fitting cooperatively with a respective one of said second connector elements to form a single connector such that said first and second concentrate holders are joined on an input side thereof with a first connector and on an output side thereof with a second connector, said first connector elements each having a first membrane closing them and spaced therefrom a piercing pin which is in communication with a first connection line and surrounded by an annular space in that is in communication with the first concentrate holder, said second connector elements being in connection with the second concentrate holder and each having a second membrane closing said second connector elements, said second connector elements cutting said first membranes when at least partly inserted into said first connector elements, and said piercing pins of said first connector elements thereafter cutting said second membranes when said second connector elements are fully inserted within said first connector elements.

15. A concentrate container unit in accordance with claim 14, further comprising a feed line which extends from the first connector to said first and second concentrate holders on said input side, and a discharge line which extends from said first and second concentrate holders to said second connector on said output side.

16. A concentrate container unit in accordance with claim 14, wherein the first membrane closing the first connector element and/or the second membrane closing the second connector element is a silicone membrane.

17. A concentrate container unit in accordance with claim 14, wherein the concentrate is a dry concentrate containing NaCl, NaHCO$_3$ and glucose or a liquid concentrate which contains as the main components the ions $K^+$, $Ca^{++}$, $Mg^{++}$ and NaCl.

18. A concentrate container unit in accordance with claim 17, wherein the liquid concentrate further contains the components citrate and HCl.

* * * * *